United States Patent [19]

Bröcker et al.

[11] Patent Number: 5,728,900
[45] Date of Patent: Mar. 17, 1998

[54] PROCESS FOR THE SELECTIVE HYDROGENATION OF BUTYNE-1,4-DIOL TO BUTENE-2-DIOL-1,4

[75] Inventors: Franz Josef Bröcker, Ludwigshafen; Rainer Becker, Bad Dürkheim; Volkmar Menger, Neustadt; Peter Stops, Altrip, all of Germany

[73] Assignee: BASF Aktiengesellschaft, Ludwigshafen, Germany

[21] Appl. No.: 608,647

[22] Filed: Feb. 29, 1996

Related U.S. Application Data

[62] Division of Ser. No. 315,922, Sep. 30, 1994, Pat. No. 5,521,139.

[30] Foreign Application Priority Data

Sep. 30, 1993 [DE] Germany ............ 43 33 293.5

[51] Int. Cl.$^6$ .................................................. C07C 29/56
[52] U.S. Cl. ............................ 568/857; 568/861; 502/314
[58] Field of Search ........................... 568/857, 861

[56] References Cited

U.S. PATENT DOCUMENTS

| | | | |
|---|---|---|---|
| 2,681,938 | 6/1954 | Lindlar | 260/611 |
| 2,953,604 | 9/1960 | Hort | 260/635 |
| 2,967,835 | 1/1961 | Hort | 252/447 |
| 4,001,344 | 1/1977 | Hoffmann et al. | 260/635 M |
| 4,388,479 | 6/1983 | Gryaznov et al. | 568/828 |
| 4,686,202 | 8/1987 | Broecker | 502/300 |
| 5,063,194 | 11/1991 | Broecker et al. | 502/314 |
| 5,521,139 | 5/1996 | Bröcker et al. | 502/314 |

*Primary Examiner*—Gary Geist
*Assistant Examiner*—Sreeni Padmanabhan
*Attorney, Agent, or Firm*—John H. Shurtleff

[57] ABSTRACT

Catalyst and process for the preparation of butene-2-diol-1,4 by the hydrogenation of butyne-2-diol-1,4 in aqueous solution over a palladium-containing fixed-bed catalyst, which is doped with lead or cadmium, in which a catalyst is used which has been made by applying Pd and Pb or Pd and Cd successively, by vapor deposition or sputtering, to a metal gauze or a metal foil acting as support material followed by forming the catalyst at an elevated temperature in air.

7 Claims, No Drawings

PROCESS FOR THE SELECTIVE HYDROGENATION OF BUTYNE-1,4-DIOL TO BUTENE-2-DIOL-1,4

This application is a division of prior application Ser. No. 08/315,922, filed Sep. 30, 1994. This application issued on May 28, 1996, as U.S. Pat. No. 5,521,139.

The invention relates to a process for the hydrogenation of butyne diol to butene diol using a wire mesh catalyst, to which palladium and lead or cadmium have been applied successively. The hydrogenation of butyne diol to butene diol is well covered in the prior art.

For example, an improved selective hydrogenation of acetylene compounds is described in GB-A 871,804 in a suspension method involving the use of a Pd catalyst which has been treated with salt solutions of the metals Zn, Cd, Hg, Ga, Bi, or Ti.

Furthermore, DE-A 2,431,929 describes a process for the preparation of butene-2-diol-1,4 by hydrogenation of butyne diol in aqueous solution over a catalyst containing Pd and one of the elements Zn or Cd and at least one of the elements Bi or Te. The catalyst support used is pumice or aluminum oxide.

Lead-doped Pd catalysts, so-called Lindlar catalysts, are usually used for the selective hydrogenation of the triple bond in precursors for vitamins and perfumes as described in U.S. Pat. No. 2,681,938 for example. In many instances these are still deactivated by means of sulfur compounds (JP-A-120,657/81) in order to increase the selectivity. Finally, DE-A 2,619,660 describes a process for the preparation of butene diol, in which butyne diol is hydrogenated in an inert solvent in the presence of a catalyst which contains metallic Pd which has been treated with carbon monoxide.

In addition, the use of a Pd/BaSO$_4$ catalyst for the preparation of butene diol is disclosed by DE-A 2,605,241.

All of the said processes for the preparation of butene diol by selective hydrogenation of butyne diol suffer from the disadvantage that a suspended catalyst is used and the catalyst must be separated from the reaction product on completion of hydrogenation by settling followed by filtration.

It has been found that the complete separation of the powdered catalyst is possible only at great expense. Traces of residual catalyst in the butene diol, however, cause considerable difficulty during subsequent processing, and consequently there has been no lack of attempts to provide a fixed-bed catalyst for the hydrogenation of the triple bond in butyne diol.

EP-A 0,412,415 describes such a fixed-bed catalyst for the hydrogenation of hydro/dehydrolinalool to hydrolinalool, which catalyst contains palladium as active ingredient and bismuth as the inhibitor.

However when butyne diol is hydrogenated to form butene diol at quantitative conversion, a Pd/Bi catalyst prepared as described in said EP-A 0,412,415 yields a hydrogenation product having an excessively high residue of 6.75% (cf. comparative example), presumably as a result of polymer formation as a secondary reaction.

It is thus the object of the present invention to provide a fixed-bed catalyst for the selective hydrogenation of butyne diol to butene diol which avoids the drawbacks of hydrogenation involving a suspended catalyst and yields a minimum of byproducts.

We have now found that the amount of residue formed in the process for the preparation of butene-2-diol-1,4 can be minimized by the hydrogenation of butyne-2-diol-1,4 in aqueous solution over a palladium-containing fixed-bed catalyst which is doped with lead or cadmium, if a catalyst is used which has been made by applying Pd and Pb or Pd and Cd successively, by vapor deposition or sputtering, to a metal gauze or a metal foil acting as support material followed by forming the catalyst at an elevated temperature in air. Catalysts prepared in this manner demonstrate increased activity and selectivity as compared with bismuth-doped palladium catalysts and the raised activity makes it possible to achieve hydrogenation at temperatures between 20° and 100° C. and preferably between 40° and 80° C. Since the formation of trans butene diol increases as the temperature rises and a high cis content is desired in the butene diol, it is advantageous when the hydrogenation can be carried out at as low a temperature as possible.

The catalysts of the invention are prepared by vapor deposition, such as sputtering of the active ingredient Pd and of the inhibitors Cd or Pd to a sheet-like or cloth-like metal support.

Particularly good results have been achieved when using metallic sheets or gauzes of materials designated by the material numbers: 1.4767, 1.4401 and 1.4301. These material numbers are taken from the "Stahl-Eisen-Liste" published by the Association of German Metallurgists, 8th Edition, pp 87, 89, and 106, Verlag Stahleisen mbH, Düsseldorf 1990. The material designated as No. 1.4767 is also known under the name of "Kanthal".

The materials having the material numbers 1.4767, 1.4401 and 1.4301 are alloy steels and have the following composition in % by weight:

| Material No. | C | Si | P | S | Cr | Al | Mo | Ni | Mn |
|---|---|---|---|---|---|---|---|---|---|
| 1,4767 | ≦0.10 | ≦1.0 | ≦0.045 | ≦0.030 | 19.0–22.0 | 4.0–6.5 | — | — | ≦1.0 |
| 1,4401 | ≦0.07 | ≦1.0 | ≦0.045 | ≦0.030 | 16.5–18.5 | — | 2.0–2.5 | 10.5–13.5 | ≦2.0 |
| 1,4301 | ≦0.07 | ≦1.0 | ≦0.045 | ≦0.030 | 17.0–19.0 | — | — | 8.5–10.5 | ≦2.0 |

The compositions are made up to 100% with iron.

These metallic support materials are pretreated by baking in the presence of oxygen, preferably atmospheric oxygen, at temperatures ranging from 600° to 1100° C. and preferably from 700° to 1000° C. and are subsequently coated with the active component and the inhibitor. Following the coating step, thermal forming is carried out in air to give the actual catalyst material. The forming step is carried out by heating the coated support material in air for from 0.5 to 2 h at temperatures ranging from 200° to 800° C. and preferably from 300° to 700° C. The catalyst material thus produced is subsequently shaped into monolithic entities by deformation. The catalyst is ready for use in the hydrogenation of butyne diol following reduction of the catalyst with hydrogen at temperatures ranging from 50° to 250° C. and preferably from 80° to 150° C., which is advantageously carried out in the reactor.

According to the invention, catalysts are used which have been prepared by vapor deposition of palladium, followed by lead or cadmium, on to the support material. This vapor deposition process is first of all effected using palladium at a rate of in general from 20 to 300 mg/m² and preferably from 40 to 200 mg/m², followed by lead at a rate of in general from 10 to 60 mg/m² and preferably from 20 to 40 mg/m² or cadmium at a rate of in general from 10 to 50 mg/m² and preferably from 15 to 30 mg/m².

The methods of vapor deposition such as the sputtering of metals in vacuo are described in detail in Handbook of Thin Film Technology, Maissel and Glang, McGraw Hill, New York, 1970, Thin Film Processes, J. L. Vossen and M. Kern, Academic Press N.Y. and in EP-A 0,198,435, to which we specifically refer.

The hydrogenation is advantageously carried out using for example a 50% strength aqueous butyne diol solution in pressure equipment by a trickle method at a steady cross-sectional throughput of from 20 to 120 and preferably of, say, 60 m³/m²·h. This throughput per cross-sectional area guarantees uniform wetting of the catalyst.

The following examples demonstrate the results obtained in hydrogenations using various support materials compared with the prior palladium/bismuth catalysts.

In the following examples the percentages relating to quantities are by weight and those relating to yields are in terms of theory.

EXAMPLE 1

A plain-woven wire gauze made of material designated by the number 1.4767 and having a mesh size of 0.18 mm and a wire diameter of 0.112 mm was baked in air for 5 h at a temperature of 1000° C. The resulting pretreated supporting gauze was then coated successively with 92 mg of palladium/m² (fabric area) and 21.3 mg of lead/m² in an electron-beam vaporizer. The coated gauze was heated in a muffle for 0.5 h in air at 600° C. in order to form the catalyst. A monolithic body was shaped from the catalyst gauze prepared in this manner. To this end, part of the gauze was corrugated by means of a toothed roller. This corrugated gauze was placed together with a smooth strip of gauze and coiled up. There was thus obtained a monolithic shaped article, which was made secure by spot welding. This catalyst was reduced with hydrogen for one hour in the hydrogenation equipment at 150° C. without pressure and, after cooling, used for the hydrogenation of a 50% strength aqueous butyne diol solution at a hydrogen partial pressure of 15 bar and a hydrogenation temperature of 60° C. The 50% strength aqueous solution was hydrogenated by a trickle method operating at a cross-sectional throughput of 60 m³/m²·h. and the space-time yield was 1.0 l/l $_{cat}$·h based on the 50% strength solution and 0.42 l/m²·h based on the catalyst gauze area. The hydrogenation product (organic portion without $H_2O$) contained 98% of butene diol having a trans butene diol content of 1.76% and 1.8% of residues.

EXAMPLE 2

A wire gauze made of the material designated by the number 1.4767 was pretreated in the manner described in Example 1 and vapor coated with 92 mg of Pd/m² and 16.2 mg of Cd/m² and subsequently baked for 0.5 h at a temperature of 300° C. Following the stage of forming a monolithic unit, a 50% strength aqueous butyne diol-solution was hydrogenated in the manner described in Example 1 at a temperature of 55° C. and a hydrogen partial pressure of 15 bar. The space-time yield was found to be 1.57 l/l$_{cat}$·h based on the solution and 0.69 l/m²·h. A butene diol content of 97.1% was found in the organic end product having a trans content of 1.12% and a residue of 1.37%.

EXAMPLE 3

V2A gauze, material No. 1.4401 having a mesh size of 200 μm and a wire diameter of 125 μm was baked for 3 h at a temperature of 850° C., the resulting pretreated gauze then being coated with 92 mg of Pd/m² and 21.3 mg of Pb/m² in the manner described in Example 1 and subsequently post-baked for 0.5 h at 300° C. Following the procedure described in Examples 1 and 2, the catalyst gauze was formed to a monolith and was used for the hydrogenation of butyne diol. The space-time yield was 1.6 l/l$_{cat}$·h based on the aqueous solution and 0.6 /l m²·h based on the catalyst gauze area. The hydrogenation product contained 98% of butene diol having a trans content of 1.7% and a residue of 1.9%.

EXAMPLE 4

As described in Example 3, a stainless steel gauze designated by material number 1.4301 and having a mesh size of 125 μm and a wire thickness of 100 μm was annealed for 3 h at a temperature of 800° C. and coated subsequently with 21.3 mg of lead/m² and 92 mg of palladium/m² (fabric area). The coated gauze was formed by heating to 300° C. in air over a period of one hour and was kept at this temperature for 30 min. Following shaping to catalyst monoliths these were tested as described in Examples 1 to 3. At a space-time yield of 1.7 l/l$_{cat}$·h and 0.62 l/m²·h, the hydrogenation yielded an organic product which contained 98% of butene diol having a trans content of 1.4% and a residue of 2%.

COMPARATIVE EXAMPLES

For comparison purposes, a palladium/bismuth catalyst was used as described in EP-A 0,412,415. To this end, the wire gauze material No. 1.4767 was pretreated in the manner described in Example 1, by baking at a temperature of 1000° C. followed by coating with 46 mg Pd/m² and 12.8 mg of Bi/m². The coated gauze was baked in air for 0.5 h at a temperature of 600° C. and then shaped into a monolith. The hydrogenation of a 50% strength aqueous butyne diol solution was carried out as described in Example 1 at a hydrogenation temperature of 120° C. The space-time yield was 1.6 l/l $_{cat}$·h and 0.7 l/m²·h based on the 50% strength solution. Analysis of the organic hydrogenation product gave a butene diol content of 93% and a residue of 6.75%.

We claim:

1. In a process for the preparation of butene-2-diol-1,4 by the hydrogenation of butyne-2-diol-1,4 in aqueous solution over a palladium-containing catalyst, the improvement which comprises:

carrying out the hydrogenation at low temperatures favoring the selective production of the cis form of said butenediol over a fixed-bed catalyst which has been prepared by using a metal gauze or metal foil as a catalyst support material onto which there has been successively applied by vapor phase deposition, first, palladium as the active catalyst component, and thereafter, at least one of the metals lead or cadmium as a catalyst inhibitor, followed by thermally forming the fully coated catalyst material at an elevated temperature in air to provide a monolithic catalyst structure, and subsequently reducing the resulting thermally formed catalyst with hydrogen at an elevated temperature.

2. A process as claimed in claim 1, wherein the selective hydrogenation is carried out at a temperature between 20° and 100° C.

3. A process as claimed in claim 1, wherein the selective hydrogenation is carried out at a temperature between 40° and 80° C.

4. A process as claimed in claim 1, wherein the metal support material has been annealed, prior to said vapor phase deposition, in air at a temperature of about 600° to 1,100° C.

5. A process as claimed in claim 1, wherein the metal support material has been coated by vapor deposition first with palladium in an amount of from 20 to 300 mg/m$^2$ and then with lead in an amount of from 10 to 60 mg/m$^2$ or cadmium in an amount of from 10 to 50 mg/m$^2$.

6. A process as claimed in claim 1, wherein the thermal forming of the coated catalyst material is carried out at a temperature of from 300° to 700° C.

7. A process as claimed in claim 1, wherein the thermally formed catalyst material is subsequently reduced with hydrogen at a temperature of between 20° and 250° C. prior to hydrogenation of the butyne-2-diol-1,4 reactant.

* * * * *